United States Patent
Arnin et al.

(10) Patent No.: US 6,966,930 B2
(45) Date of Patent: Nov. 22, 2005

(54) FACET PROSTHESIS

(75) Inventors: Uri Arnin, Kiryat Tivon (IL); Yuri Sudin, Lod (IL); Michael Tauber, Tel Aviv (IL)

(73) Assignee: Impliant Ltd., Netanya (IL)

( * ) Notice: Subject to any disclaimer, the term of this patent is extended or adjusted under 35 U.S.C. 154(b) by 0 days.

(21) Appl. No.: 10/735,645

(22) Filed: Dec. 16, 2003

(65) Prior Publication Data

US 2005/0085912 A1    Apr. 21, 2005

Related U.S. Application Data

(60) Provisional application No. 60/512,193, filed on Oct. 20, 2003.

(51) Int. Cl.[7] ................................................ A61F 2/44
(52) U.S. Cl. ..................................... 623/17.11; 606/61
(58) Field of Search .............................. 606/61, 63, 76, 606/78; 623/17.11, 17.12, 17.13, 17.15, 17.16, 623/23.47, 23.5

(56) References Cited

U.S. PATENT DOCUMENTS

| | | | | |
|---|---|---|---|---|
| 4,911,718 A | * | 3/1990 | Lee et al. ..................... | 623/17 |
| 5,147,404 A | * | 9/1992 | Downey ........................ | 623/17 |
| 5,171,284 A | * | 12/1992 | Branemark ................... | 623/21 |
| 5,306,310 A | * | 4/1994 | Siebels ........................ | 623/17 |
| 5,571,191 A |  | 11/1996 | Fitz | |
| 6,099,565 A | * | 8/2000 | Sakura, Jr. ..................... | 623/8 |
| 6,296,664 B1 | * | 10/2001 | Middleton ............... | 623/17.15 |
| 6,342,076 B1 | * | 1/2002 | Lundborg ................ | 623/21.15 |
| 6,436,142 B1 | * | 8/2002 | Paes et al. ............... | 623/17.15 |
| 6,451,057 B1 | * | 9/2002 | Chen et al. .............. | 623/17.15 |
| 6,610,094 B2 | * | 8/2003 | Husson .................... | 623/17.16 |
| 6,660,037 B1 | * | 12/2003 | Husson et al. ........... | 623/17.11 |
| 2003/0004572 A1 |  | 1/2003 | Goble et al. | |

FOREIGN PATENT DOCUMENTS

WO     WO 01/30248     5/2001

* cited by examiner

Primary Examiner—Kevin Shaver
Assistant Examiner—David Comstock
(74) Attorney, Agent, or Firm—Dekel Patent Ltd.; David Klein

(57) ABSTRACT

An article including a facet prosthesis at least partially mounted in a lumen artificially formed between superior and inferior halves of a facet joint, and an elastomeric cushioning element disposed in the facet prosthesis.

5 Claims, 6 Drawing Sheets

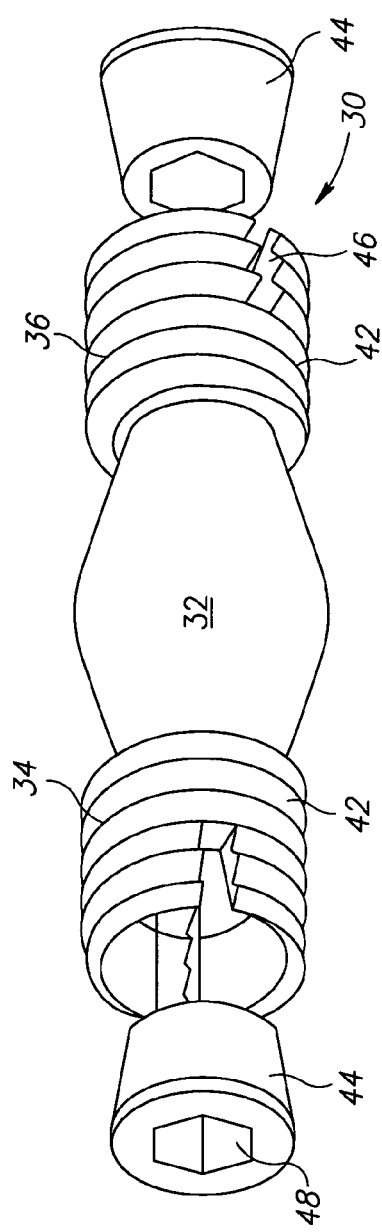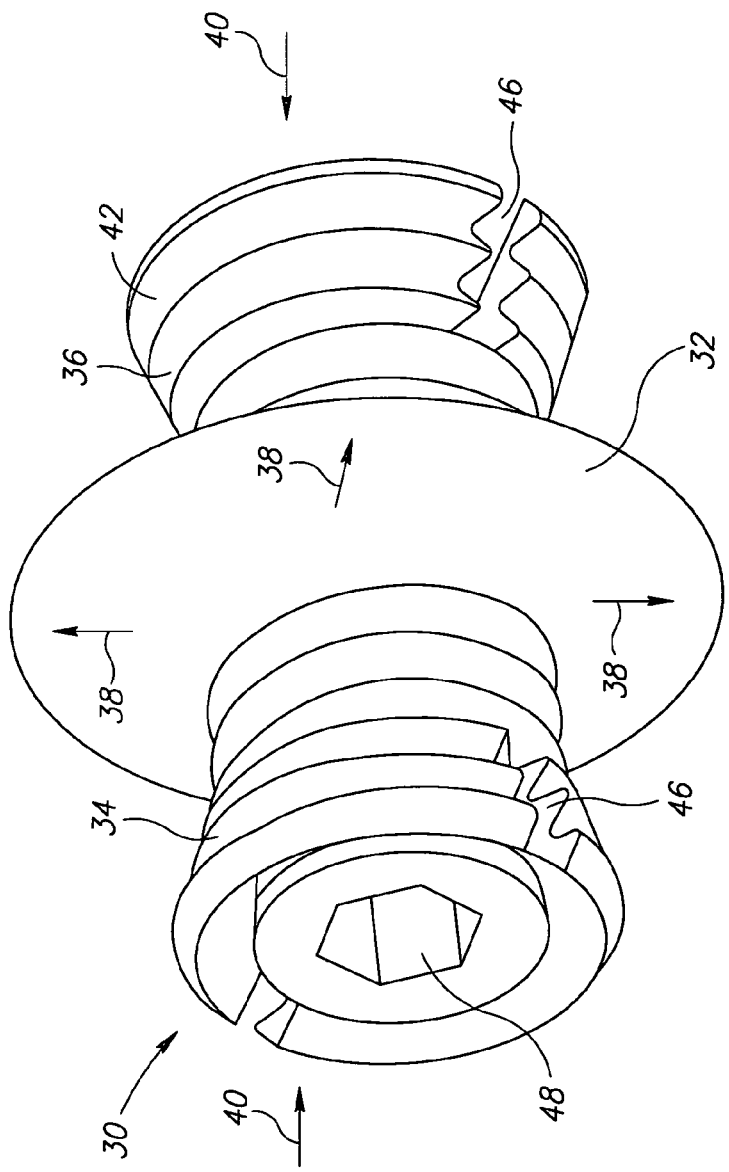
FIG.2A
FIG.2B

FACET PROSTHESIS

CROSS-REFERENCE TO RELATED APPLICATIONS

This application claims priority under 35 USC §119 to U.S. Provisional Patent Application Ser. No. 60/512,193, filed on Oct. 20, 2003, which is incorporated herein by reference.

FIELD OF THE INVENTION

The present invention relates to human prostheses, and more particularly to prostheses for a spinal facet joint.

BACKGROUND OF THE INVENTION

Traumatic, inflammatory, metabolic, synovial, neoplastic and degenerative disorders of the spine can produce debilitating pain that can have severe socioeconomic and psychological effects. One of the most common surgical interventions today is arthrodesis, or spine fusion, of one or more motion segments, with approximately 300,000 procedures performed annually in the United States. Clinical success varies considerably, depending upon technique and indications, and consideration must be given to the concomitant risks and complications. For example, it has been shown that spine fusion decreases function by limiting the range of motion for patients in flexion, extension, rotation, and lateral bending. Furthermore, it has been shown that spine fusion creates increased stresses and, therefore, accelerated degeneration of adjacent non-fused motion segments. Additionally, pseudoarthrosis, as a result of an incomplete or ineffective fusion, may reduce or even eliminate pain relief for the patient. Also, the fusion device, whether artificial or biological, may migrate out of the fusion site.

Recently, several attempts have been made to recreate the natural biomechanics of the spine by use of an artificial disc. Artificial discs provide for articulation between vertebral bodies to recreate the full range of motion allowed by the elastic properties of the natural intervertebral disc that directly connects two opposed vertebral bodies.

However, the artificial discs proposed to date do not fully address the mechanics of motion of the spinal column. In addition to the intervertebral disc, posterior elements called facet joints help to support axial, torsional, and shear loads that act on the spinal column. Furthermore, facet joints are diarthroidal joints that provide both sliding articulation and load transmission features. The effects of their absence as a result of facetectomy has been observed to produce significant decreases in the stiffness of the spinal column in all planes of motion: flexion and extension, lateral bending, and rotation. Furthermore, contraindications for artificial discs include arthritic facet joints, absent facet joints, severe facet joint tropism or otherwise deformed facet joints.

SUMMARY OF THE INVENTION

The present invention is directed to facet joint prostheses, as is described more in detail hereinbelow.

There is thus provided in accordance with an embodiment of the present invention an article including a facet prosthesis at least partially mounted in a lumen artificially formed between superior and inferior halves of a facet joint, and an elastomeric cushioning element disposed in the facet prosthesis.

The facet prosthesis can include one or more of the following features. For example, the elastomeric cushioning element can include first and second mechanical fasteners at opposite ends thereof, which are attachable to superior and inferior halves of the facet joint. The elastomeric cushioning element can expand radially outward upon axial movement of the first and second mechanical fasteners towards each other. The first and second mechanical fasteners can include an expandable sleeve member in which is disposed a wedge, wherein insertion of the wedge into the expandable sleeve member expands the expandable sleeve member radially outwards. The expandable sleeve member can include an axial slit formed therein. The elastomeric cushioning element can include a plurality of elastomeric balls disposed in the lumen and sealed in the lumen with end caps. The elastomeric cushioning element can include a wire coil coated with an elastomeric material disposed in the lumen and sealed in the lumen with end caps. The wire coil can be constructed of a shape memory alloy.

BRIEF DESCRIPTION OF THE DRAWINGS

In the drawings:

FIGS. 2A and 2B are pictorial illustrations of a facet prosthesis in an uncompressed and compressed from, respectively;

DESCRIPTION OF EMBODIMENTS

Figure 1A:
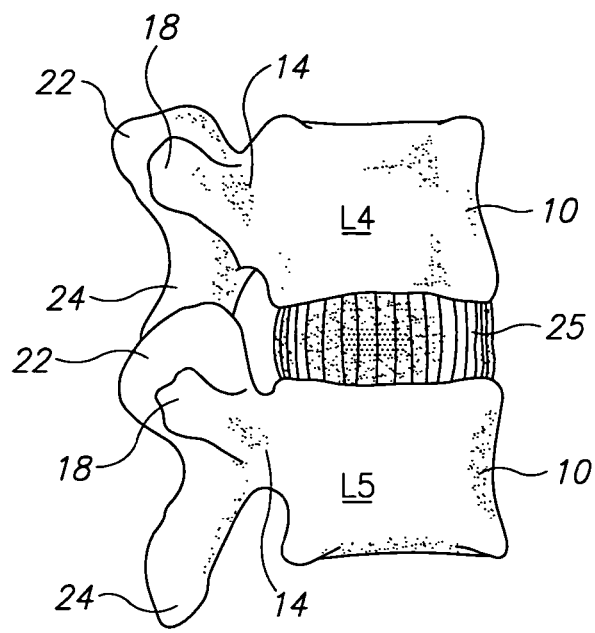
FIGS. 1A and 1B are pictorial illustrations of part of a human spine including a facet joint.
Figure 1B:
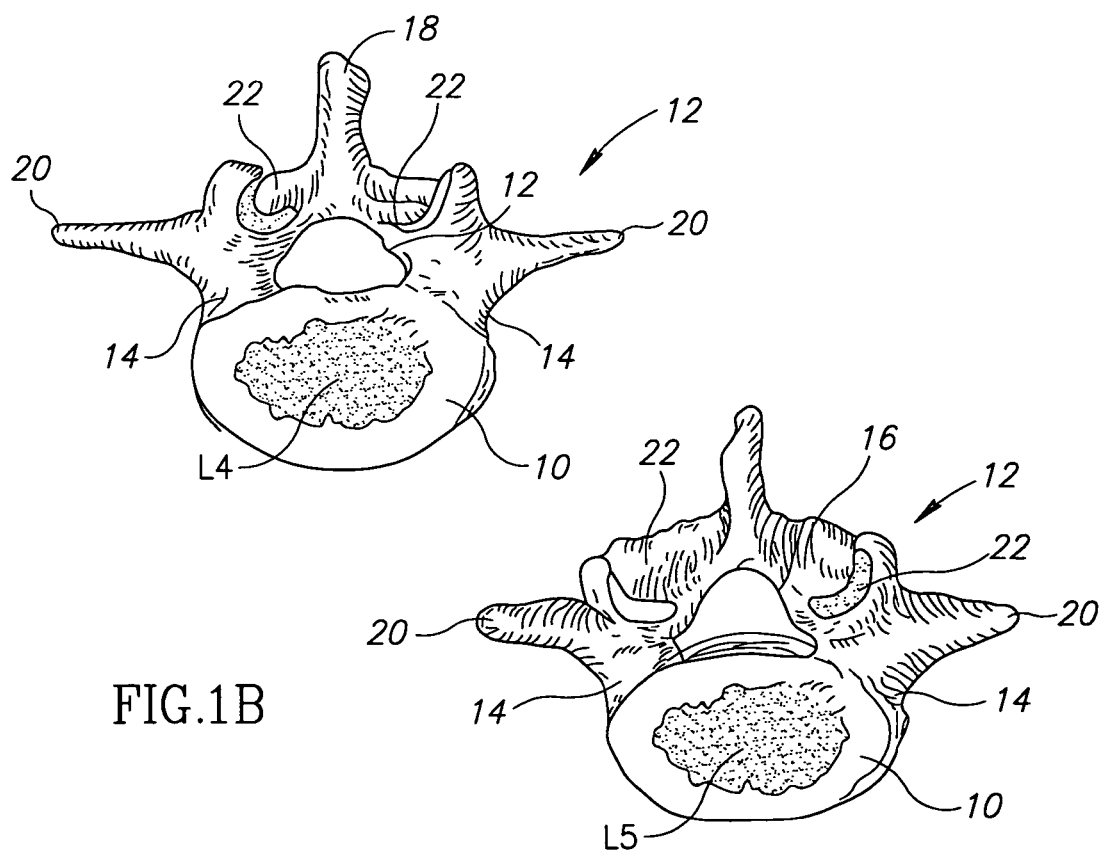

Reference is now made to FIGS. 1A and 1B, which illustrate a structure of a human spine, in particular the lumbar vertebrae including a facet joint.

FIGS. 1A and 1B illustrate the fourth and fifth lumbar vertebrae L4 and L5, respectively, in a lateral view (while in anatomic association) and in a superior view (separately). The lumbar vertebrae (of which there are a total of five) are in the lower back, also called the "small of the back."

As is typical with vertebrae, the vertebrae L4 and L5 are separated by an intervertebral disk 25. The configuration of the vertebrae L4 and L5 differ somewhat, but each (like vertebrae in general) includes a vertebral body 10, which is the anterior, massive part of bone that gives strength to the vertebral column and supports body weight. The vertebral arch 12 is posterior to the vertebral body 10 and is formed by the right and left pedicles 14 and lamina 16. The pedicles 14 are short, stout processes that join the vertebral arch 12 to the vertebral body 10. The pedicles 14 project posteriorly to meet two broad flat plates of bone, called the lamina 16.

Seven other processes arise from the vertebral arch. Three processes, called the spinous process 18 and two transverse 20 processes, project from the vertebral arch 12 and afford attachments for back muscles, forming levers that help the muscles move the vertebrae. The remaining four processes, called articular processes, project superiorly from the vertebral arch (and are thus called the superior articular processes 22) and inferiorly from the vertebral arch (and are thus called the inferior articular processes 24). The superior and inferior articular processes 22 and 24 are in opposition with corresponding opposite processes of vertebrae superior and inferior adjacent to them, forming joints, called zygapophysial joints or, in short hand, the facet joints or facets. Facet joints are found between adjacent superior and inferior articular processes along the spinal column and the facet joints permit gliding movement between the vertebrae L4 and L5.

The facet joints can deteriorate or otherwise become injured or diseased, causing lack of support for the spinal column, pain, and/or difficulty in movement.

As described herein, a facet joint has a superior half and an inferior half, with cartilage therebetween. The superior half of the joint is formed by the vertebral level below the joint, and the inferior half of the joint is formed by the vertebral level above the joint. For example, in the L4–L5 facet joint, the superior half of the joint is formed by structure on the L-5 vertebra, and the inferior half of the joint is formed by structure on the L-4 vertebra.

Reference is now made to FIGS. 2A and 2B, which illustrate a facet prosthesis 30, constructed and operative in accordance with an embodiment of the present invention. Facet prosthesis 30 may include an elastomeric cushioning element 32, constructed of an elastomeric material, such as but not limited to, polyurethane or polyurethane containing materials, silicone or silicone containing materials, polyethylene based elastomers, hydrogels, and polypropylene containing materials, and the like, or any combination thereof. First and second mechanical fasteners 34 and 36 may be provided at opposite ends of the cushioning element 32, which are attachable to the superior and inferior halves 22 and 24 (FIGS. 1A and 1B) of the facet joint, as described hereinbelow.

The elastomeric cushioning element 32 may initially have an oblong shape (FIG. 2A) prior to implantation in the facet joint. The elastomeric cushioning element 32 may then expand radially outwards (as indicated by arrows 38 in FIG. 2B) upon axial (e.g., compressive) movement of the first and second mechanical fasteners 34 and 36 towards each other (as indicated by arrows 40 in FIG. 2B).

In one non-limiting example, first and second mechanical fasteners 34 and 36 may be constructed as an expandable sleeve member 42 in which is disposed a wedge 44. Insertion of the wedge 44 into expandable sleeve member 42 in the direction of arrow 40 expands expandable sleeve member 42 radially outwards in the direction of arrows 38. Wedges 44 may be part of a threaded fastener, which may be screwed into expandable sleeve member 42, similar to an expansion bolt (also called an anchor bolt or molly bolt) used to anchor objects on soft walls or ceilings. The expandable sleeve member 42 may have an axial slit 46 formed therein to facilitate outward expansion thereof. Wedges 44 may have a hexagonal socket 48 for turning with an Allen key and the like. The expandable sleeve member 42 may be made of a plastic, such as but not limited to, nylon, DELRIN or polyurethane, for example, or from a metal, such as but not limited to, stainless steel. Wedge 44 may be made of metal, such as but not limited to, stainless steel, titanium alloy, cobalt chromium alloys, ceramics, or other hard, rigid materials, or may be made of a plastic, such as but not limited to, nylon, DELRIN or polyurethane.

Figure 3:
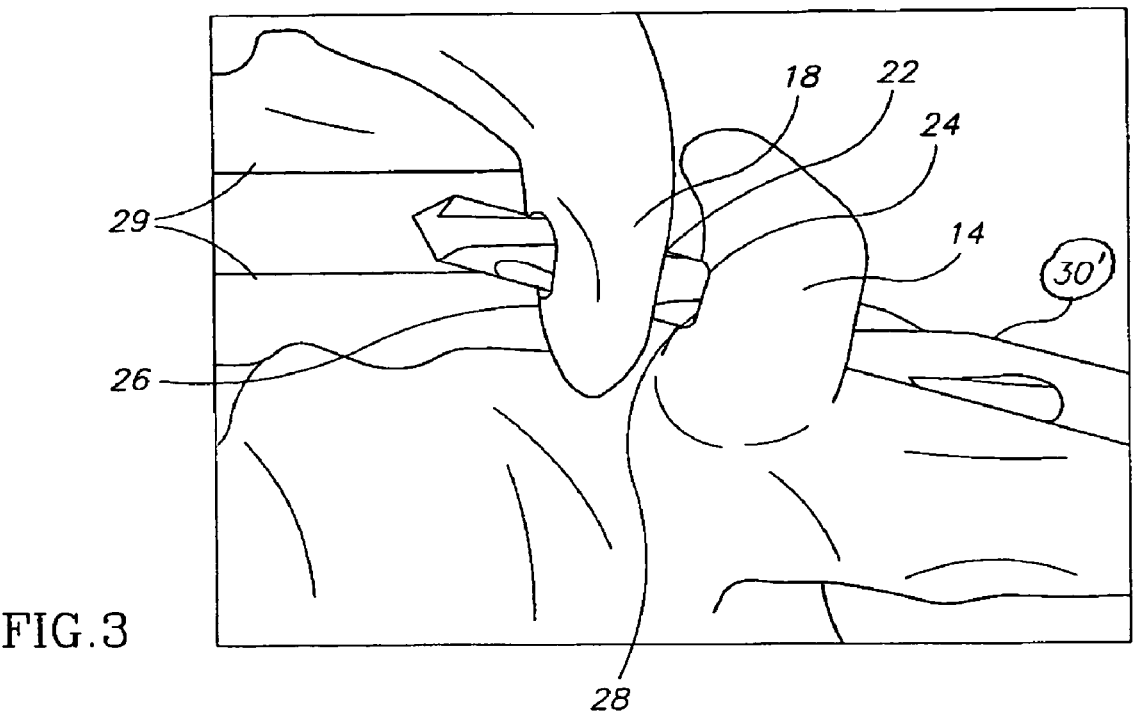
FIG. 3 is a pictorial illustration of lumens being formed through aligned superior and inferior processes of adjacent vertebrae.

Reference is now made to FIG. 3, which shows a side view of a facet joint prior to placement of a facet prosthesis within the joint.

When adjacent vertebra 29 are aligned, and the superior articular facet 22 of one vertebra faces the inferior articular facet 24 of an adjacent vertebra facet, two lumens, or holes, 26 and 28 may be formed, such as by drilling with a drill 30', through the aligned superior and inferior processes of the adjacent vertebrae 29.

Figure 4:
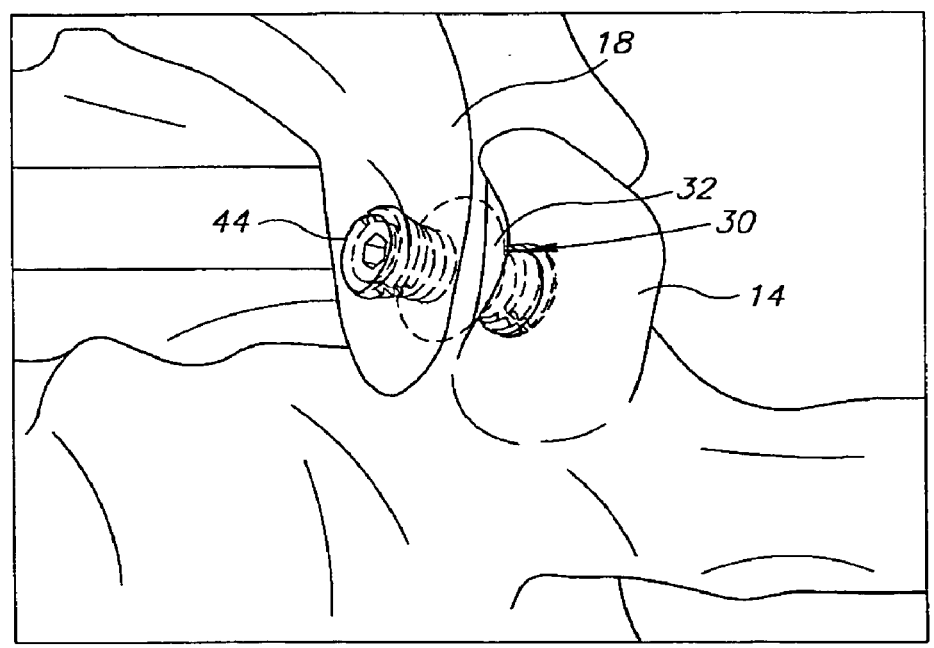
FIG. 4 is a pictorial illustration of the facet prosthesis of FIGS. 2A and 2B implanted within a facet joint between two adjacent vertebrae.

The facet prosthesis 30 may then be inserted in the lumens 26 and 28. During insertion, the sleeve member 42 has not yet been expanded, so that the prosthesis 30 has a smaller diameter than the lumens 26 and 28 to aid in insertion of the prosthesis. Afterwards, the sleeve member 42 is expanded by the above-described action of wedges 44, thereby anchoring facet prosthesis 30 in the lumens 26 and 28 formed in the facet joint, as seen in FIG. 4. In this installed orientation, the elastomeric cushioning element 32 is in its compressed form (expanded radially outward).

Figure 5:
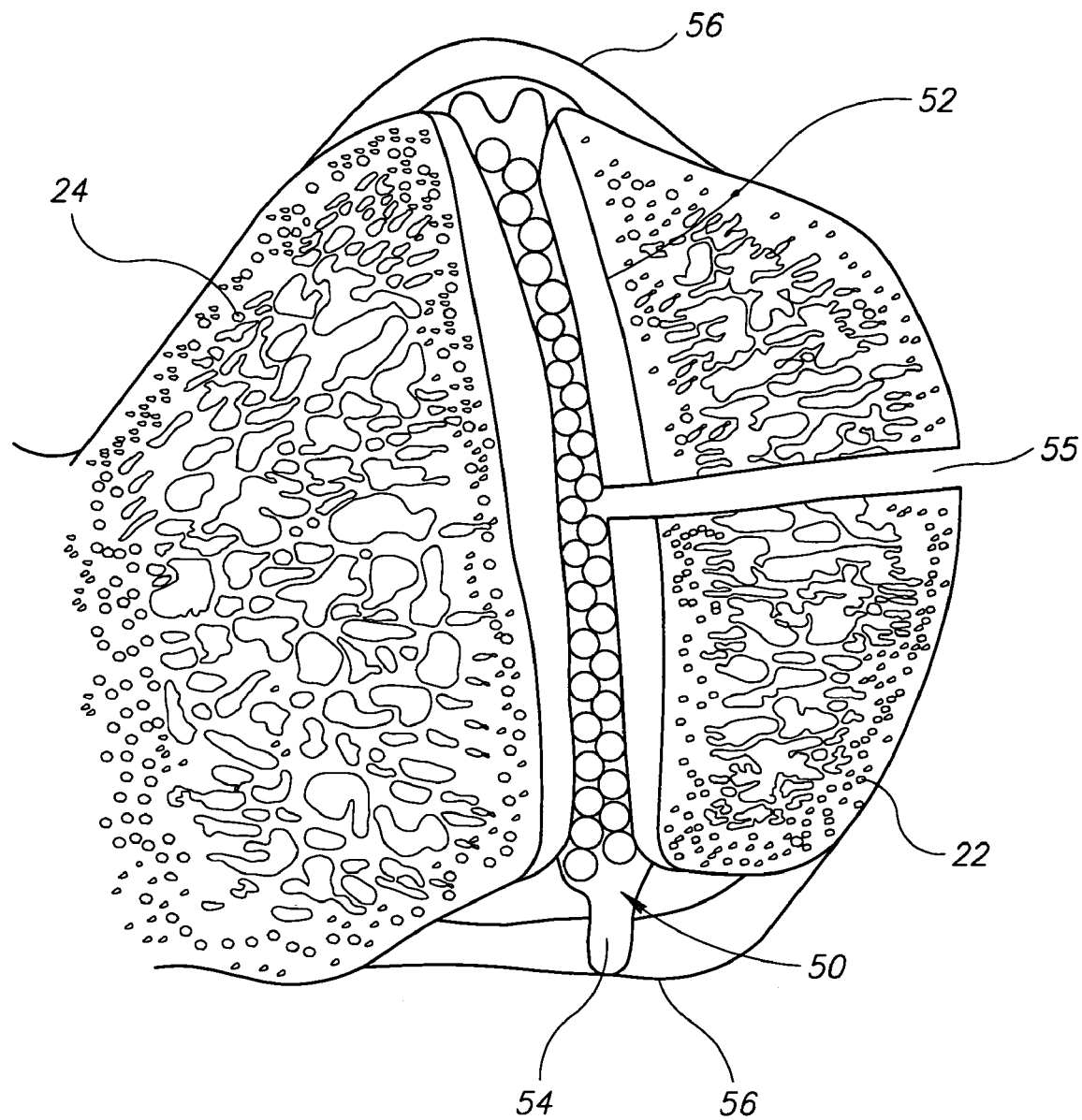
FIG. 5 is a pictorial illustration of a facet prosthesis including an elastomeric cushioning element, constructed and operative in accordance with another embodiment of the present invention.

Reference is now made to FIG. 5, which illustrates a facet prosthesis 50, constructed and operative in accordance with another embodiment of the present invention. In facet prosthesis 50, the elastomeric cushioning element includes a plurality of elastomeric balls 52 disposed in a lumen 54, which may be formed by drilling through cartilage between superior and inferior halves 22 and 24. Access may be gained to lumen 54 alternatively by drilling an access hole 55 directly through superior half 22. The elastomeric balls 52 may be sealed in lumen 54 with end caps 56. Elastomeric balls 52 may be constructed of an elastomeric material, such as but not limited to, polyurethane or polyurethane containing materials, silicone or silicone containing materials, polyethylene based elastomers, hydrogels, and polypropylene containing materials, and the like, or any combination thereof, and may have any suitable size. The term "balls" encompasses not only spherical shaped objects, but also oblong, ellipsoidal, prismatic and other shapes that may be placed in lumen 54.

Figure 6A:
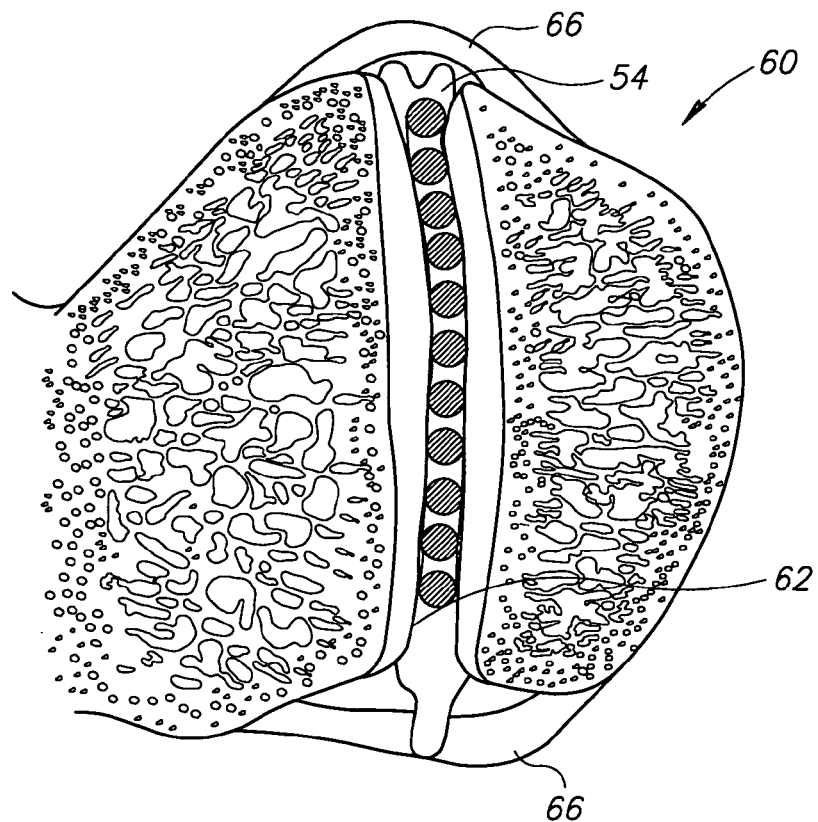
FIGS. 6A and 6B are pictorial illustrations of a facet prosthesis including an elastomeric cushioning element, constructed and operative in accordance with yet another embodiment of the present invention, respectively showing the prosthesis installed in a facet joint and showing a wire coil coated with an elastomeric material that forms part of the prosthesis.
Figure 6B:
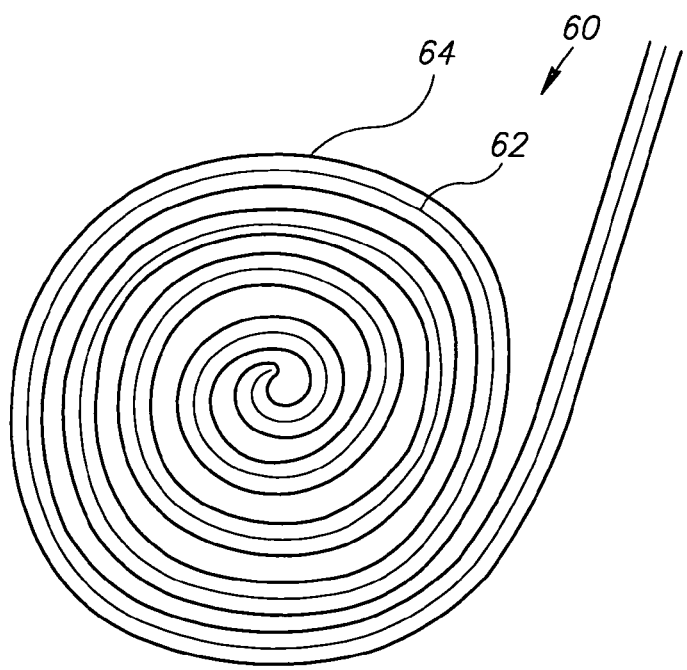

Reference is now made to FIGS. 6A and 6B, which illustrate a facet prosthesis 60, constructed and operative in accordance with yet another embodiment of the present invention. In facet prosthesis 60, the elastomeric cushioning element includes a wire coil 62 coated with an elastomeric material 64, such as but not limited to, polyurethane or polyurethane containing materials, silicone or silicone containing materials, polyethylene based elastomers, hydrogels, and polypropylene containing materials, and the like, or any combination thereof. The wire coil 62 may be constructed of a shape memory alloy, such as but not limited to, NITINOL.

The elastomeric coated wire coil 62 may be disposed in lumen 54, which may be formed by drilling through cartilage between superior and inferior halves 22 and 24. The elastomeric coated wire coil 62 may be sealed in lumen 54 with end caps 66.

Figure 7A:
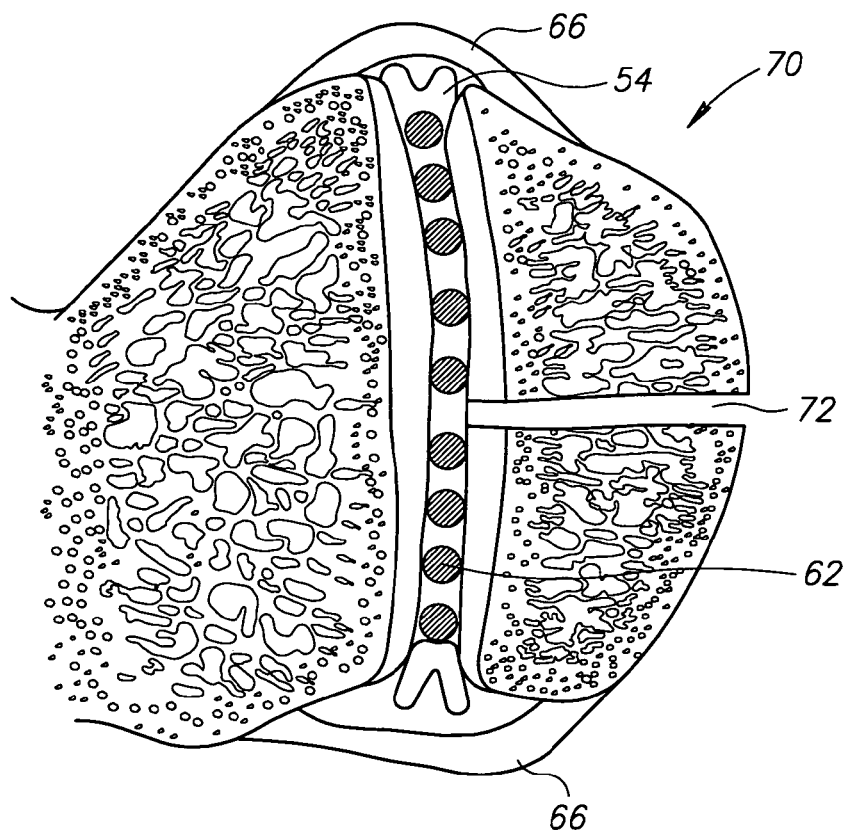
FIGS. 7A and 7B are pictorial illustrations of a facet prosthesis including an elastomeric cushioning element, constructed and operative in accordance with still another embodiment of the present invention, respectively showing the prosthesis installed in a facet joint and showing a wire coil coated with an elastomeric material that forms part of the prosthesis.
Figure 7B:
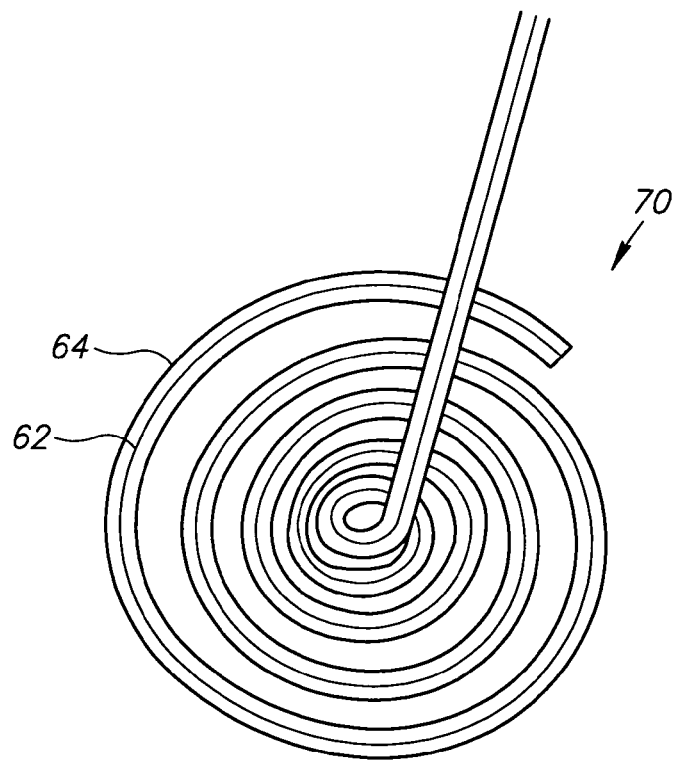

FIGS. 7A and 7B illustrate a facet prosthesis 70, very similar to facet prosthesis 60, except that facet prosthesis 70 may be introduced into lumen 54 through a passageway 72 formed by drilling directly through superior half 22. Both facet prostheses 60 and 70 may have any shape or size, such as but not limited to, round, square, oblong, elliptical, triangular, etc.

Although various specific implementations have been described, it is evident that many alternatives, modifications and variations will be apparent to those skilled in the art. Accordingly, other alternatives, modifications, and variations that fall within the scope of the following claims.

What is claimed is:

1. An article comprising:
    a facet prosthesis at least partially mounted in a lumen artificially formed between superior and inferior halves of a facet joint; and
    an elastomeric cushioning element disposed in said facet prosthesis, wherein said elastomeric cushioning element includes first and second mechanical fasteners at opposite ends thereof which are attachable to superior and inferior halves of the facet joint,
    wherein said first and second mechanical fasteners comprise an expandable sleeve member, the facet prosthesis further comprising a wedge insertable into said expandable sleeve member, wherein the sleeve expands radially upon insertion of the wedge into the sleeve.

2. The article according to claim 1, wherein said expandable sleeve member has an axial slit formed therein.

3. The article according to claim 1, wherein said elastomeric cushioning element includes a wire coil coated with an elastomeric material disposed in said lumen and sealed in said lumen with end caps.

4. The article according to claim 3, wherein said wire coil is constructed of a shape memory alloy.

5. An article comprising:
    a facet prosthesis at least partially mounted in a lumen artificially formed between superior and inferior halves of a facet joint; and
    an elastomeric cushioning element disposed in said facet prosthesis, wherein said elastomeric cushioning element includes a plurality of elastomeric balls disposed in said lumen and sealed in said lumen with end caps.

* * * * *